United States Patent [19]

Petersen

[11] Patent Number: 4,520,797
[45] Date of Patent: Jun. 4, 1985

[54] COLLATERAL LIGAMENT RETRACTOR

[76] Inventor: Thomas D. Petersen, 9680 Alto Dr., La Mesa, Calif. 92041

[21] Appl. No.: 514,162

[22] Filed: Jul. 15, 1983

Related U.S. Application Data

[63] Continuation of Ser. No. 269,792, Jun. 3, 1981, abandoned.

[51] Int. Cl.³ .............................................. A61B 17/02
[52] U.S. Cl. ...................................... 128/20; 128/345
[58] Field of Search ...................... 128/3, 17, 20, 80 C, 128/126, 341, 345

[56] References Cited

PUBLICATIONS

"Standard Surgical Instruments", Cat. Murray Baumgartner Sur. Instr. Co., Dec. 1934.

Primary Examiner—Edward M. Coven
Assistant Examiner—Max F. Hindenburg
Attorney, Agent, or Firm—Sherman & Shalloway

[57] ABSTRACT

A collateral ligament retractor includes a first member having a cupped arcuate finger member for insertion into the knee joint, along and partly around the tibal plateau and a curved portion extending from the finger outward around the ligament extending back substantially in the same direction as the finger and including a downwardly extending pivoted elongated arm extending to a position behind the knee above the calf with a second member being of similar design but larger to accommodate the everted patella positioned around the opposite ligament and a tension member in the form of a coil spring connected to the outer end of the arms of the members for biasing the arms toward one another for holding the ligaments in a retracted position.

5 Claims, 5 Drawing Figures

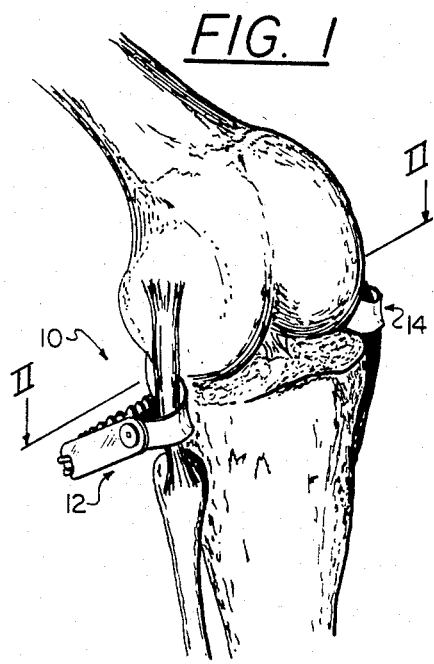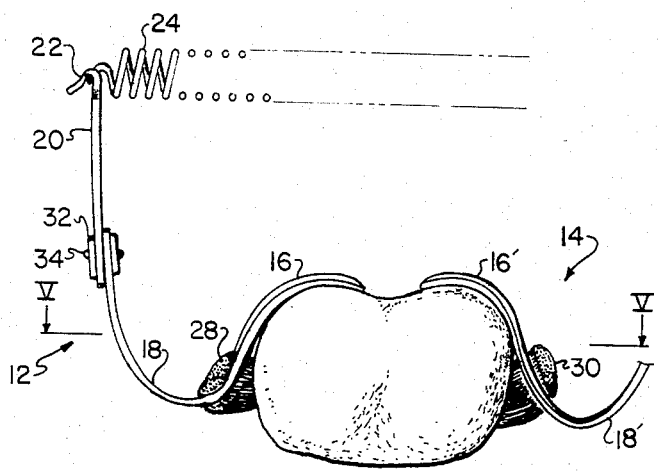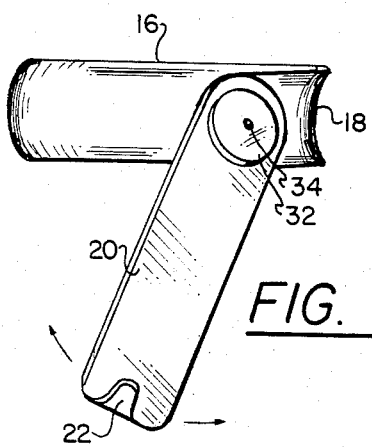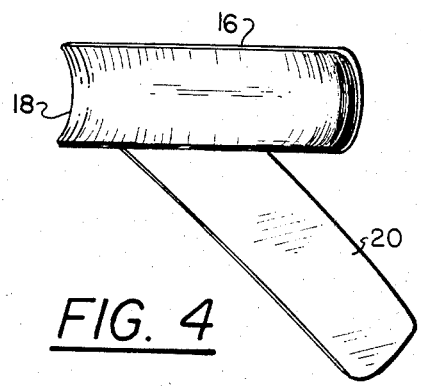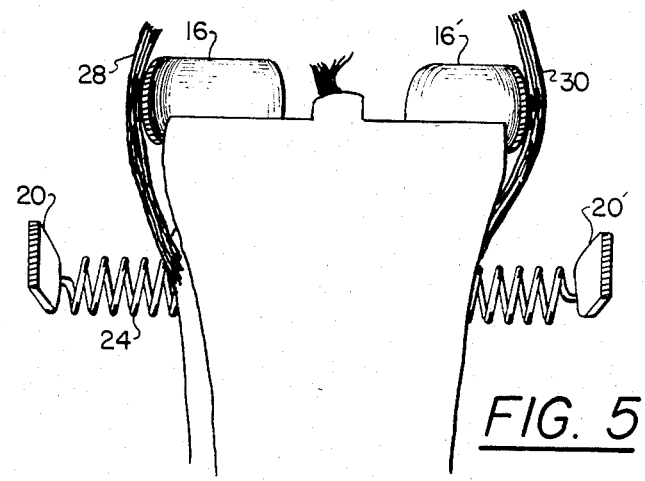

COLLATERAL LIGAMENT RETRACTOR

This is a continuation of application Ser. No. 269,792 filed June 3, 1981, now abandoned.

BACKGROUND OF THE INVENTION

The present invention relates to surgical instruments and tools and pertains particularly to a collateral ligament retractor.

These instruments provide access to the knee joint for performing surgery. An appropriate incision is made along forward of the knee joint with the skin and flesh being parted to provide access to the joint. The flesh and the collateral ligaments are typically pulled or retacted laterally to expose the joint and held in this position by a hand held instrument referred to as a retractor. These hand held retractors are held either by the surgeon or his assistant to maintain exposure of the joint to permit surgery to be performed. Such methods and instruments and the additional hand required tend to interfere with access by the surgeon for performing the necessary surgery.

It is therefore desirable that simple and effective means be available for retracting the flash and collateral ligaments and to free the hands of the surgeon and his assistant to perform their task.

SUMMARY AND OBJECT OF THE INVENTION

It is therefore the primary object of the present invention to provide an improved collateral ligament retractor.

In accordance with the primary aspect of the present invention a collateral ligament retractor comprises a pair of retractor members of different sizes to accommodate the anatomy, each, including a curved finger portion and a curved pivoted arm extending downwardly toward the axis of rotation of the knee with a tension member extending between the respective arm of the retractor members for retaining them in place.

BRIEF DESCRIPTION OF THE DRAWING

The above and other objects and advantages of the present invention will become apparent from the following description when read in conjunction with the drawings wherein:

FIG. 1 is a perspective view showing the retractor in use.

FIG. 2 is a section view taken generally on line II—II of FIG. 1.

FIG. 3 is a side elevation view of one retractor member.

FIG. 4 is a cross elevation view of the member of FIG. 3.

FIG. 5 is a section view taken generally on line V—V of FIG. 2.

DESCRIPTION OF A PREFERRED EMBODIMENT

Referring to FIG. 1, there is illustrated a collateral ligament retractor in accordance with the invention shown in position in use. For the purposes of clarity, only bone structure and the collateral ligaments will be illustrated. However, it should be understood that during the normal operation, flesh, muscles, and bandages, as well as ligaments, and the everted patella will surround the knee structure with an incision exposing only the front portion of the knee as seen in FIG. 1.

The retractor assembly designated generally by the numeral 10 consists of a non-patellar side retractor member 12 and a patellar side retractor member 14. For the purposes of illustration only, the non-petallar member 12 will by fully illustrated and described with it being understood that the patellar size member 14 is substantially identical except for side and minor curvature differences. The retractor member 12 has a generally S-configuration as shown in FIG. 2 including a long curved cupped finger member 16 that is adapted to extend along and curve around the tibia curving therealong for approximately 3¾ linear inches to the pivot point. This finger portion 16 is cupped and as will be seen in FIG. 5 as curving around both in a horizontal as well as vertical direction with a compound curvature for fitting around the tibal plateau. The patellar side member is shown with identical reference numerals primed. A curved arm portion 18 having a curvature at the juncture of the arm and finger on the order of approximately 1 to 1¾ inches in diameter, curves outward from the finger extending back approximately 120 degrees of slightly in excess of 120 degrees from the finger, curving back and joining with elongated pivoted arm 20 at the pivot extending downward at a variable angle having a range of approximately 360 degrees. A tension spring 24 extends between the arms 20 and 20' and corresponding hook (not shown) of arm 20' connect at hook 22. It will be appreciated that, in viewing the FIG. 1 and 2, embodiments that the space between the arm 20 and finger 16 is filled with the opposed collateral ligaments 28 and 30, flesh, everted patella and bandages or the like (not shown). The above described material is pulled away from the front of the knee joint and held in a retracted position as illustrated, by the collateral retractors in position as shown in FIG. 1 and 2, with the tension spring 24 in position. These function as levers to retract the ligaments, etc. and are held in position by the tension of spring 24 without the aid of the surgeon or assistant and frees the hands of the surgeon and his assistant for the operation. The downwardly pivoted arms 20 and 20' of the retractor members enables the arms and tension member 24 to be positioned so that the knee can be flexed without interfering with the retractor assembly. While these arms 20 can be straight back in line with finger 16 with a U-shaped tension member, the pivoted angled arm with coil spring is preferred. The arms 20 and 20' are connected to the respective retractor member by means of a pivot joint including a pair of opposed washers 32 and a pin 34. The pivot pins and axis preferably align just back of the knee joint substantially tangentially to the cupped fingers 16 and 16'. These pivoting arms allow self-adjustment and permit flexing and extending of the leg or joint as needed. Stops may be added to limit the extent of pivotal movement of the arm if desired.

This above described assembly provides an effective hands off retractor that frees the hands of the surgeon for the operation. It will also be appreciated that the retractor members can be utilized individually (i.e., individually manipulable) and can be hand held. The unique shape and curvature thereof, provides a simple and effective retractor that is easily and conveniently utilized for different sizes of knee structure, a retractor of the size described above, is somewhat universal and can be used on substantially any size knee. The above described retractor is of a size having sufficient structural strength and dimension to perform its function and yet, is small enough to be utilized without interfering with the surgery procedures. The finger portion 16 and 16' that is illustrated in FIG. 5 for example, can slide sufficiently outward to permit removal of the upper portion of the tibal plateau. These fingers 16 and 16' should be positioned about center of the joint as shown.

The retractor is of course preferably constructed of flat stock of a high grade of stainless steel to permit surgical use thereof and permit sterilization as needed. As explained above, each set of retractors will normally include one slightly larger than the other to accommodate the everted patella. Also, the sets therselves can vary in size to accommodate anatomical differences. For a somewhat average size system, the main body member 12 sould be about 3 and 15/16 inches (about 10 centimeters) in linear length, whereas member 14 should be about 4 and 15/16 inches (about 12.5 centimeters). The arms 20 and 20' should both be about 2.0 inches in length. The curvature 18 should be about $\frac{1}{2}$ inch in radius with the curvature 18' about $\frac{3}{4}$ inches. The width of the member should be about $2\frac{1}{4}$ inch and $2\frac{1}{2}$ inch respectively.

It will also be appreciated that the arms 20 and 20' can also be rigid and may extend at an angle downward from the fingers. They may also extend back in the plane of the finger. Theses variations however, are not as desirable for most applications.

While I have illustrated and described my invention by means of specific embodiments, it is to be understood that numerous changes and modifications may be made therein without departing from the spirit and scope of the invention as defined in the appended claims.

Having described my invention, I now claim:

1. A collateral ligament retractor assembly for retracting a pair of collateral ligaments for aiding and providing acess to a knee structure for knee surgery, comprising:

a pair of substantially symmetrical individually manipulable retractor members, each retractor member defined by generally S-shaped lever means including curved finger means formed at one end thereof for independent insertion between a collateral ligament and a tibia plateau and partially encircling and extending behind and engaging the tibia plateau thereby providing fulcrum means comprising a pivot point about which said retractor member pivots in use, and including curved arm means curving around past said one end to a position outside the collateral ligament and terminating at a position behind and to one side of said one end and said tibia, and tension means connected between the arm means of said retractor members behind a knee structure after said retractor members have each been independently inserted in place said tension means pivoting said retractor members about their fulcrum means thereby holding the ligaments in a retracted position away from the tibia for providing access thereto.

2. The collateral ligament retractor assembly of claim 1 wherein each of said lever means includes pivoting arm means pivotally connected to an end of said curved arm means remote from said finger means and pivotable to variable positions out of the common plane including said finger means and said curved arm means.

3. The collateral ligament retractor of claim 2 wherein said tension means is a coil spring releasably connected between outer ends of each of said pivoting arm means.

4. The collateral ligament retractor of claim 1 wherein said curved finger means is generally cupped in configuration by curving about two separate axes.

5. A collateral ligament retractor assembly for retracting a pair of collateral ligaments for providing access to a knee for knee surgery, comprising:

a pair of substantially symmetrical individually manipulable retractor members, each retractor member defined by generally S-shaped lever means having curved finger means at one end for independent insertion between a collateral ligaments and a tibia plateau and partially encircling and extending behind and engaging the tibia plateau thereby providing fulcrum means defining a pivot point about which said retractor member may pivot in use, and each retractor member including curved arm means for curving around the collateral ligament and past said one end to a position outside the collateral ligament and extending to and terminating at a positions behind and to one side of the tibia, and of said one end, said curved arm means includes a pivoting arm pivotally connected to and end of said curved arm means remote from said finger means and pivotable to variable positions out of a common plane of said finger means and said curved arm means, and coil spring means releaseably connected between the respective pivoting arms of said retractor members after said retractor members have each been independently inserted in place between the respective ligaments and tibia, said coil spring means biasing said retractor members and causing them to pivot about their fulcrum means and holding the ligaments in a retracted position away from the tibia to provide access thereto.

* * * * *